United States Patent [19]

Tu

[11] Patent Number: 5,779,715
[45] Date of Patent: Jul. 14, 1998

[54] LEAD EXTRACTION SYSTEM AND METHODS THEREOF

[75] Inventor: Hosheng Tu, Tustin, Calif.

[73] Assignee: Irvine Biomedical, Inc., Irvine, Calif.

[21] Appl. No.: 901,500

[22] Filed: Jul. 28, 1997

[51] Int. Cl.$^6$ ............................................. A61B 17/50
[52] U.S. Cl. ............................................. 606/108; 606/50
[58] Field of Search ............................................. 607/101, 113, 607/116; 606/108, 50

[56] References Cited

U.S. PATENT DOCUMENTS

| | | | |
|---|---|---|---|
| 5,522,875 | 6/1996 | Gates et al. | 607/127 |
| 5,556,424 | 9/1996 | Hocherl et al. | 607/116 |
| 5,620,451 | 4/1997 | Rosborough | 606/108 |
| 5,632,749 | 5/1997 | Goode et al. | 606/108 |

OTHER PUBLICATIONS

H J Smith et al. "Five-Years Experience with Intravascular Lead Extraction" Pacing and Clinical Electrophysiology 17, No. 11, 2016–2020 (1994).

H J Smith et al. "Major Factors in Interventional Lead Extraction Techniques" A poster presented at ACC 42nd Annual Meeting, Anaheim, CA (Mar. 1993).

*Primary Examiner*—William E. Kamm

[57] ABSTRACT

An improved lead extraction system having multiple-jaw cutting edge that is useful for extraction and removal of unwanted lead by a minimal invasive procedure. A lead extraction system suitable for radiofrequency ablation of scar tissues surrounding the implanted lead comprises a catheter sheath having a distal end, a proximal end and at least one lumen extending therebetween, wherein a locking stylet is provided. In one embodiment, the lead extraction system has fluid infusion and irrigation means at its distal tip section and a set of ablation electrodes for loosening the target tissue by applying radiofrequency energy and cooled fluid to said electrode and its contacted tissue.

20 Claims, 4 Drawing Sheets

LEAD EXTRACTION SYSTEM AND METHODS THEREOF

FIELD OF THE INVENTION

The present invention generally relates to improved system for cardiac lead extraction. More particularly, this invention relates to a catheter system and methods for removing an implanted endocardial pacemaker lead or an implanted transvenous defibrillation lead from the heart of a patient.

BACKGROUND OF THE INVENTION

Symptoms of abnormal heart rhythms are generally referred to as cardiac arrhythmias. An abnormally rapid rhythm being referred to as tachycardia, while the arrhythmia rates below the normal rhythm are termed bradycardia. Various factors affect the human heart rate and contribute to changes of rate from what is termed the normal sinus rate range. The rates generally range in adults from 60 to 100 beats per minute. The heart includes a number of normal pathways which are responsible for the propagation of electrical signals from upper to lower chamber necessary for performing normal systole and diastole function.

Treatment of arrhythmias may be accomplished by a variety of approaches, including drugs, surgery, implantable pacemakers/defibrillators, and catheter ablation. While drugs may be the treatment of choice for many patients, they only mask the symptoms and do not cure the underlying causes. Surgical and catheter-based treatments can only cure some simple cases. Implantable devices correct the arrhythmia and prevent it from occurring unexpectedly.

Cardiac pacemakers, chronically implanted within a patient's body, and connected to the heart by at least one lead, are frequently used to control bradycardiac conditions. Recently, implantable cardioverter-defibrillators, also implanted chronically in a patients' body and connected to the heart by at least one lead, can be used to control tachyarrhythmias and life-threatening fibrillations. There are generally two different types of body implantable leads used with cardiac pacemakers: one type which requires surgery to expose the myocardial tissue whereby an electrode is affixed to the epicardial tissue, and another type which can be inserted through a body vessel, such as a vein, into the heart where an electrode contacts the endocardiac tissue. In the second type, the endocardial lead is often secured to the heart through the endocardial lining by a helix, hook, or tines affixed to the distal end of the lead. When the end of the lead contacts the lining of the heart at a desired location, the lead may be secured in place by deploying a lead securing means, such as screwing the helix into the heart tissue, anchoring the hook or engaging the tines.

Similarly, cardioverter defibrillators have used both epicardial leads, that is, leads with electrodes attached to the outside of the heart, and endocardial leads, that is, leads inserted into the heart through a body vessel.

With either pacing or defibrillation endocardial leads, fibrotic tissue may eventually encapsulate the leads, especially in areas where there is low velocity blood flow. When small diameter veins through which the lead passes become occluded with fibrotic tissue, separating the lead from the vein is difficult and can cause severe damage to or destruction of the vein. Furthermore, separation may not be possible without constricting the movement of the lead.

In most cases, an endocardial lead will outlast its associated implanted device. However, the lead may become inoperative or another type of lead may be required. Frequently, the existing lead is left in place and an additional lead is implanted, rather risk removal of the old lead, now bonded to the surrounding tissue. Leaving the implanted lead in place, however, particularly in the heart, may further restrict the operation of various heart valves through which the lead passes. If several leads are left in place, the operation of the heart and its efficiency may be impaired.

In addition, infection may occasionally develop in or around a lead, requiring surgical removal. In some cases, surgical removal may involve open heart surgery with its accompanying complications, risks, and costs. These risks are significant for the endocardial pacemaker lead. Because the endocardial defibrillation lead is larger and more complex, the complications associated with the removal of a defibrillation lead can be even greater.

Extraction of chronically implanted leads has been difficult in the past. The problems may include lead fragility and scar tissue encountered along the vein as well as within the heart. Intravascular countertraction techniques using locking stylets and sheaths via the implant vein, or sheaths, snares, and retrieval baskets via the femoral vein have been described in the literature. Among them, scar tissue was the primary reason for partial or failed removal of a lead. Scare tissue was usually present in multiple locations; the venous entry/subclavian area and the ventricle were the most frequent sites.

Several methods for removal of pacemaker leads have heretofore been proposed. One method involves a lead removal tool that utilizes a hollow, rigid tube and beveled rod tip for engaging and deforming the coil structure of the heart lead. However, if such a lead could not be removed because of some complication, the tip of the tool was nevertheless locked in place and could not be removed from the lead. Consequently, both the tool and the lead would have to be surgically removed. Moreover, the rigid tube of the tool could easily puncture a blood vessel or a heart cavity wall.

Another method for transvenously extracting a lead involved manual manipulation without the use of an external tool. Such a method is not possible if the lead has become encapsulated in a blood vessel. Moreover, the method puts excessive strain and tension on the polyurethane or silicone insulation surrounding most pacemaker leads. Should the lead break, the broken inner coil and insulation could damage the heart or surrounding blood vessels. Surgical removal of the broken lead would be imperative. Moreover, if the pacemaker lead included tines, a cork screw, or other fixation device at the tip, pulling on the lead could seriously damage the wall of the heart.

Another technique has been proposed in U.S. Pat. No. 4,943,289. This method generally includes the use of a stiffening stylet which can be inserted into the lead and which engages the inner coil of the lead near the tip, allowing tension to be applied through the stiffening stylet close to the tip of the lead. The technique also uses a pair telescopic flexible tubes which are slid over the lead to free fibrotic connections until the tubes are close to the distal tip of the lead. In a related U.S. Pat No. 5,632,749, Goode et al. teach an anchoring project or expandable means associated with the apparatus for lead extraction.

Another method has been proposed in U.S. Pat. No. 5,620,451. In this patent, Rosborough teaches the use of a flexible coil of flattened ribbon, whereby a cutting surface is provided at the distal end of the coil. It is also disclosed that the coil is radiopaque so that its use may be observed in the body by fluoroscopy or other suitable means.

Of particular interest to the present invention are radiofrequency (RF) ablation protocols which have proven to be highly effective in tissue ablation while exposing a patient to minimal side effects and risks. Radiofrequency energy is also used in cutting the tissue, or separating implant parts and other substrates. By a combination of the mechanical force and the radiofrequency energy, extraction and removal of an implanted lead becomes feasible and less difficult.

After the exact location of a target tissue is identified, the ablation catheter may still not easily approach the target site even with assistance of an internal viewing means. This viewing situation may turn into a nightmare when an internal viewing approach becomes prohibitive or unavailable during procedures. An external ultrasonic imaging capability therefore becomes in need so that ablation is not taking place in an inappropriate location. The fluoroscope time can be substantially reduced when an external ultrasonic imaging is used instead. In the U.S. Pat. No. 4,794,931, there has been disclosed a catheter and system which can be utilized for ultrasonic imaging. However, there is no disclosure to how such a catheter and system can be utilized in conjunction with a lead extraction system with irrigation capabilities to achieve the desired ultrasonic imaging and ultimately the desired ablation.

There is therefore a need for an RF ablation system with multiple-jaw cutting edge that is useful for extraction and removal of undesired lead by minimally invasive procedures. It would be desirable for such a system to surround the tip section of an implanted lead and utilize sharp ends of said edge from symmetrical positions against the lead to cut the target tissue for improved ablation treatment and lead removal.

SUMMARY OF THE INVENTION

In general, it is an object of the present invention to provide an improved system for lead removal of both heart pacemaker leads and cardioverter-defibrillator endocardial leads. It is another object of the present invention to provide an improved lead extraction system with multiple-jaw electrodes means which can be used in ablating a desired tissue mass, such as scar tissue or fibrotic attachment surrounding an implanted lead in a minimally invasive manner. It is another object of the present invention to provide a lead extraction system with ultrasonic visual markers. It is another object of the present invention to provide a lead extraction system to extract a lead after the scar tissue is cut loose. It is another object of the present invention to provide a lead extraction system to remove a lead by a locking stylet. It is another object of the present invention to provide a lead extraction system to irrigate the scar tissue site during the lead extraction.

In one embodiment, a lead extraction system comprises a delivery catheter sheath with distal and proximal ends and at least one lumen extended therebetween. A handle is attached to the proximal end of the delivery catheter sheath. A semi-flexible, strong locking stylet is located within the lumen of said delivery catheter sheath. The locking stylet is made of strong, durable material, such as high-strength stainless steel and has a cross-sectional shape and stiffness sufficient to add mechanical strength to said delivery catheter sheath in removing the lead from the implanted site. The locking stylet is controlled by a locking deployment mechanism at the handle. In normal operations a locking stylet is pushed forward to engage it with the lead wire at the distal end of the lead system and lock the engagement action by the locking deployment mechanism.

In another embodiment, the delivery catheter sheath has an electrode deployment means. The electrode deployment means includes a retractable tip section, comprising a set of deployable jaw electrodes means, each having a sharp end and/or sharp edge. In one embodiment, the sharp end is a straight edge. In an alternate embodiment, the sharp end comprises plurality of sharp points. In a further embodiment, the sharp end comprises a slightly curved edge. In general, the sharp end and sharp edge have a conductive surface for RF energy delivery while the remaining portion of said electrodes has insulative body or surface coating. The tip section has a non-deployed state when it is positioned in the delivery catheter sheath. This non-deployed state is maintained during the insertion operation of the lead extraction system into a patient and during withdrawal of the system from a patient.

The tip section has a distended deployed state when it is advanced out of the distal end of said delivery catheter sheath. Deployment of the tip section is accomplished by a pushing action on the push-pull mechanism at the handle. Each electrode of the deployed tip section has a preformed shape so that each electrode would extend radially outwardly to its respective side of the delivery catheter sheath when deployed. The degree of deployment is controlled by the pushing action at the push-pull mechanism on the handle and is proportional to the pushing distance on the push-pull plunger which is quantifiable.

The deployed electrodes define an ablation target of the scar or the tissue covered implanted lead. The sharp end of each electrode is positioned at the circumferential base of a target tissue and is pointed at an angle which is appropriate for that electrode to advance toward the target tissue when the tip section is gradually retracted relative to the catheter sheath. The retraction operation of the tip section is accomplished by pushing down the delivery catheter sheath relative to the tip section of said multiple-jaw electrodes means so that the tips of said jaw electrodes firmly contact and grasp the target tissue during an ablation procedure. The degree of retraction is mainly controlled by the pulling action at the push-pull mechanism on the handle.

A conducting wire which is soldered to the base of the multiple-jaw electrodes means passes through the lumen of the catheter sheath and the interior void of the handle and is thereafter soldered to a contact pin of the connector at the proximal end of the handle. Therefrom, the conducting wire is connected to an external RF generator for ablation energy delivery.

The delivery catheter sheath having a tip section under a non-deployed state is inserted into the body through a natural body opening by sliding over an existing lead wire. By using an ultrasonic viewing setup, the markers on the delivery catheter sheath can be employed to locate said lead extraction system. After the system approaches the target tissue mass to be treated, the tip section is deployed by being pushed out of the delivery catheter sheath from a push-pull mechanism at the handle. Once positioned, the sharp ends of the multiple-jaw electrodes means encircle symmetrically the circumferential base of the tissue mass. By a simultaneous or alternate mode, gradually pushing forward the delivery catheter sheath against the tissue mass and applying RF energy, the target tissue mass is loosened as a result of a combination of the RF energy and mechanical cutting force of the sharp ends and/or edges of the jaw electrodes.

A fluid source is positioned at one end of the catheter sheath for supplying a fluid flow through a lumen of said catheter sheath to the tip section which has a fluid vent opening. Therefore at ablation time, the tip section with multiple-jaw electrodes means is positioned against the tissues to be ablated. The fluid is continuously or intermittently supplied through the opening to cover and rinse the tissue contact site of the electrodes so that the impedance rise at the contact site is substantially reduced. The appropriate fluid flow rate for fluid irrigation is preferably in the range of 5 cc/min to 20 cc/min. By cooling off the electrode during RF energy delivery results in optimal ablation efficiency and a desired cutting loose the scar tissue surrounding the implanted lead.

A fluid conveying lumen is associated with the elongate catheter sheath, and is preferably disposed within a separate lumen of the catheter sheath along the longitudinal axis thereof. The lumen is adapted to communicate with a fluid supply source to convey fluid from the source and through the lumen to be discharged through the opening of the tip section and diffuse out of the tip section containing multiple-jaw electrodes.

The invention also comprises a method and system for controlling the flow rate of fluid through the lumen to optimize the cooling effect of the energy delivering electrodes means of the lead extraction system. The control system preferably regulates the flow rate based on signals representative of the temperature of the catheter tip and/or tissue impedance.

Another object of the invention is to provide a lead extraction system and methods in which it is possible to view the area to be ablated prior to ablation to ensure that ablation is being carried out in an appropriate location. The delivery catheter sheath is encoded with plurality of markers which are visible to ultrasonic energy. The markers have been provided in the form of encapsulated air bubbles.

In a further embodiment, the material of the electrodes is selected from the group of platinum, iridium, gold, silver, stainless steel, and Nitinol. After the lead and its surrounding tissue is made loosen, the locking stylet is used to engage the lead with the lead extraction system and the lead is removed by said system thereafter.

The system and methods of the present invention have several significant advantages over known lead extraction system or methods. In particular, the set of multiple jaw electrodes having ablation capabilities and the delivery catheter sheath with ultrasonic imaging capabilities of this invention results in a more accurate means for ascertaining the area to be ablated and a more effective means for removing the lead from the implanted site.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
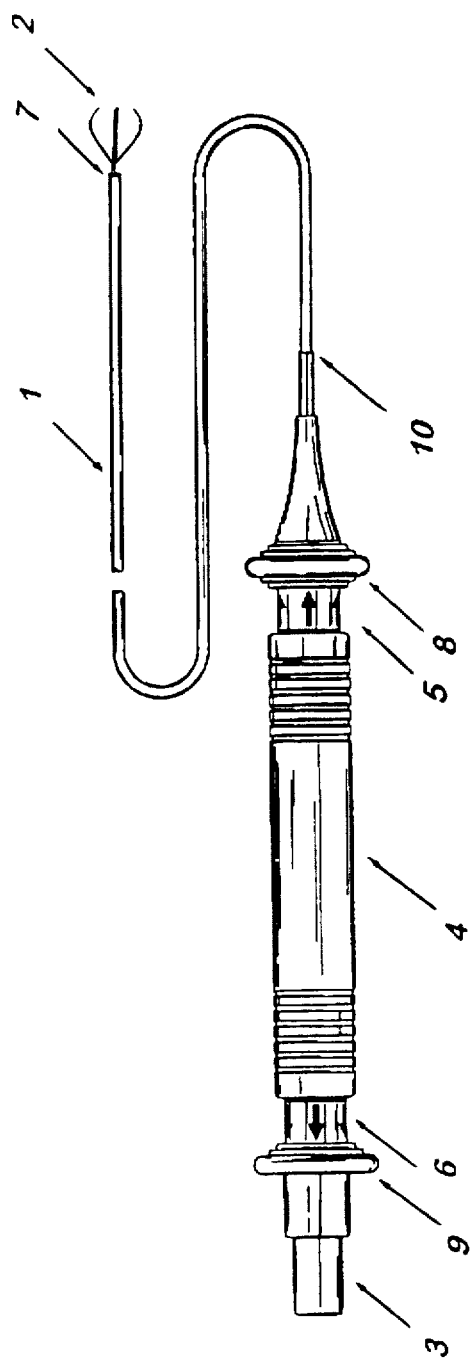
FIG. 1 is an overall view of a lead extraction system having multiple-jaw electrodes means at its distal tip section constructed in accordance with the principles of the present invention.

A lead extraction system constructed in accordance with the principles of the present invention comprises: a delivery catheter sheath having a distal end, a proximal end and at least one lumen extended therebetween. FIG. 1 shows an overall view of the lead extraction system having a delivery catheter sheath 1 with a distal end 7 and a proximal end 10. A handle 4 is attached to the proximal end 10 of said catheter sheath 1. A tip section 2 comprising multiple-jaw electrodes means is disposed at the distal end 7, wherein the electrode means is connected to a flat wire means within the lumen of the catheter sheath and is thereafter attached to a push-pull mechanism 5 on the handle 4. A pushing plunger 8 of the push-pull mechanism is used to control the degree of pushing action. The distal end of said flat wire comprises a tip section 2 with an outwardly extended multiple-jaw electrodes means. The flat wire serves as a conducting means for the electrodes means to be connected to an external RF generator. Said flat wire means with sufficient stiffness also serves as a mechanical support in advancing the lead extraction system during insertion operation and during RF ablating operation.

An insulated conducting wire which is soldered to the proximal end of said flat wire means passes through the interior void of the handle 4 and is thereafter soldered to a contact pin of the connector 3 at the proximal end of said handle 4. From there, the conducting wire is connected to an external RF generator for RF energy transmission.

Figure 2:
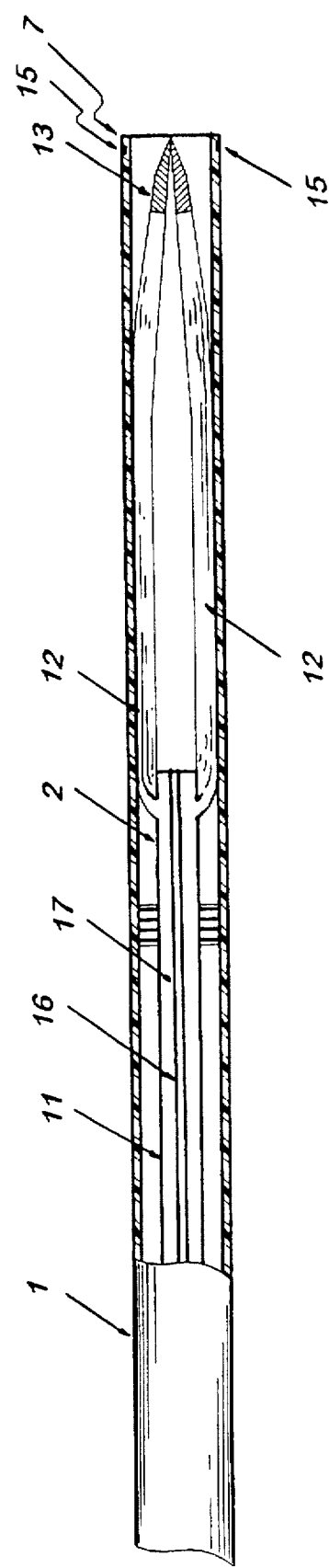
FIG. 2 is a close-up view of the retractable tip section of a lead extraction system at nondeployed state.

FIG. 2 is a close-up view of the retractable tip section at non-deployed state. The flat wire means 11, having a retractable tip section 2 comprising multiple-jaw electrodes means, is located within the lumen of the delivery catheter sheath 1. A set of deployable electrodes constitutes the farther distal end of said tip section 2. The non-deployed state is maintained during system insertion into a patient and system withdrawal from a patient. Under non-deployed state, the electrodes 12 of said tip section 2 which have a preformed shape are held inside the delivery catheter. In another alternate embodiment, a torsion spring (not shown) which is located at the joint between the base of said tip section 2 of the flat wire and the deployable electrodes 12 is an alternate embodiment to extend outwardly said electrodes when deployed. Said torsion spring is positioned in a way that moderate spring force pushes the electrodes outwardly when deployed. The flat wire may optionally be a hollow wire.

In a further embodiment, the lead extraction system may further comprise a stylet locking mechanism 6 at the handle 4 for controlling the advancement and locking activities of the locking stylet 16 of the delivery catheter sheath 1. The stylet locking plunger 9 of the locking mechanism 6 at the handle 4 is used to control the degree of the advancement of the locking stylet 16 of the delivery catheter sheath 1 inside the lead lumen 17. The stylet locking mechanism on a lead extraction system is well-known to those who are skilled in the art.

Figure 3:
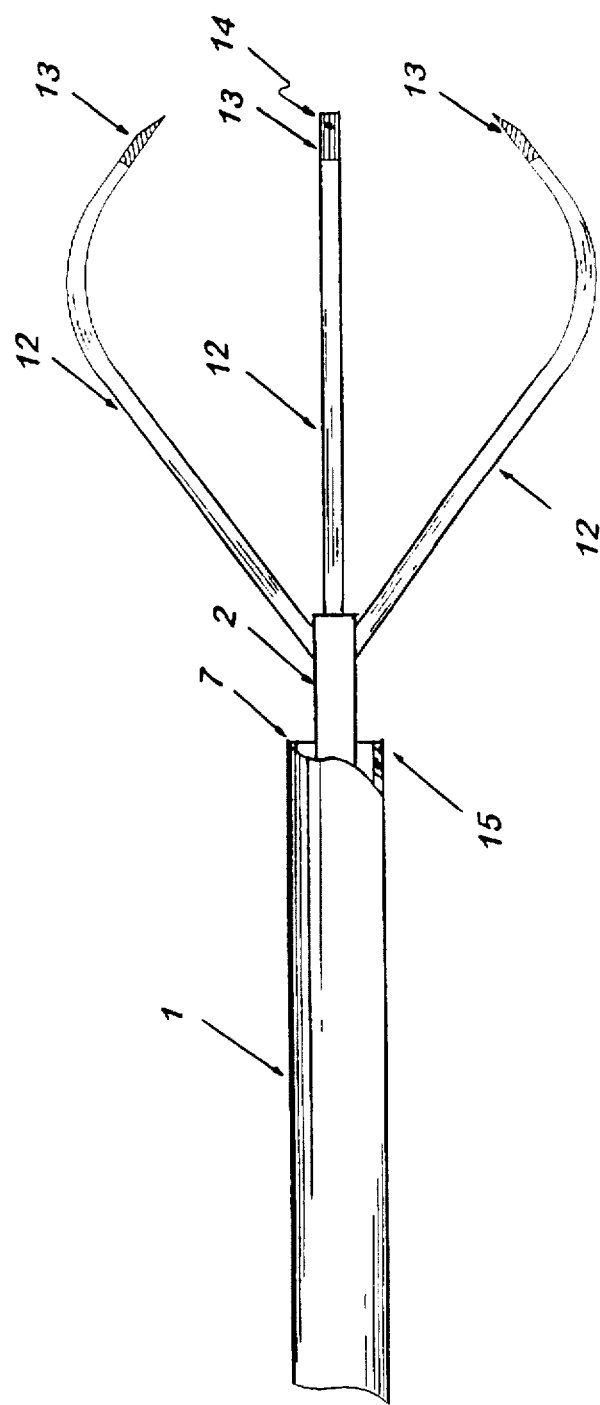
FIG. 3 is a close-up view of the retractable tip section of a lead extraction system at fully deployed state.

FIG. 3 shows a close-up view of said retractable tip section at fully deployed state. The tip section 2 has a distended deployed state when it is advanced out of the distal end 7 of said delivery catheter sheath 1. Deployment of the tip section is accomplished by a pushing action on a push-pull mechanism 5 at the handle 4. Because of its preformed shape, the jaw electrodes 12 of said distal tip section 2 extend outwardly to their respective sides of said catheter sheath 1 when deployed. In the meantime, the tips 13 of said deployed electrodes 12 point inwardly, essentially perpendicular to the target tissue.

In an additional embodiment, the lead extraction system further comprises a temperature sensing and close-loop temperature control mechanism for the electrode having a temperature sensor at the tissue contact site 14 of one electrode 12. Temperature sensing wires (not shown) along with a thermocouple or thermistor means is provided to transmit the temperature data from the tissue contact site to an external temperature measuring and control apparatus (not shown). An algorithm is equipped for the ablation system so that a close-loop temperature control is effective and the temperature data is relayed to an external RF generator (not shown) for controlled energy delivery.

Figure 4:
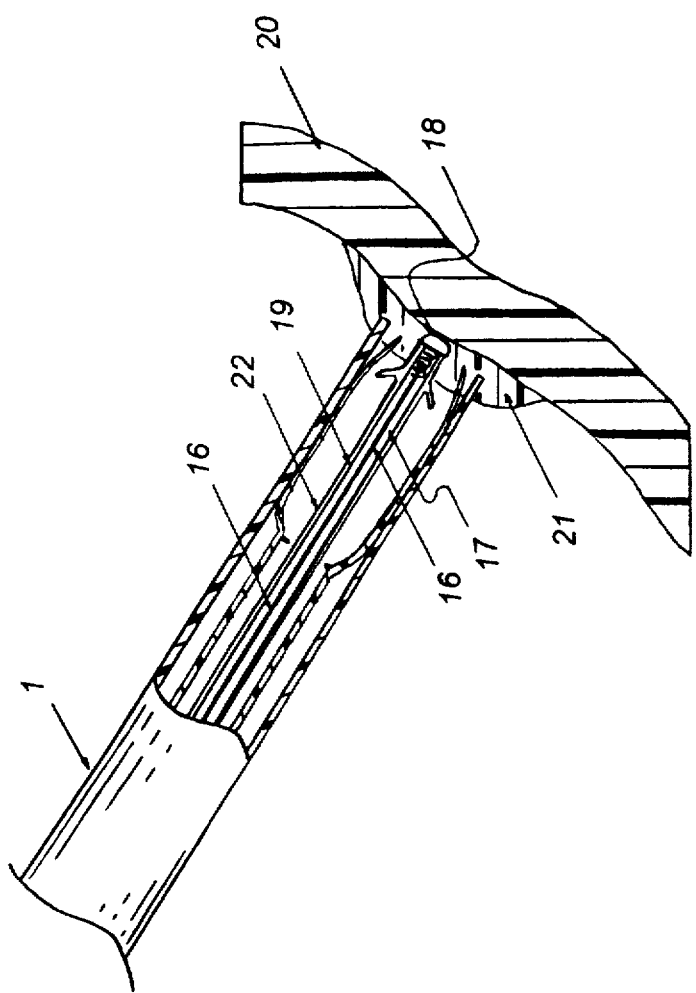
FIG. 4 is a close-up view of the lead extraction operation of the lead extraction system.

FIG. 4 is a close-up view of the lead extraction operation of the lead extraction system. An implanted lead 18 with lead coil 19 contacts the endocardial tissue 20 while scar tissue 21 surrounds the base of the lead 18. The lead system includes a lead coil 19, lead lumen 17, and lead insulation 22. The locking stylet 16 is controlled by a stylet locking mechanism at the handle 4. The sharp end 13 on each of the multiple-jaw electrodes means may be a straight edge, or a slightly curved edge. The remaining body of said electrode is made of or surface coated with an RF insulating material except the front sharp end 13, where a temperature sensor 14 is located.

In order to enhance the ablation positioning of said lead extraction system, the very distal portion in the proximity of distal end 7 of the delivery catheter sheath 1 is encoded with markers 15 (in FIG. 2 and 3) which are visible to external ultrasonic energy. Such markers 15 are provided in the form of encapsulated air bubbles. Several markers 15 are placed in a way so that the exact location of the delivery catheter sheath 1 is visible to an external ultrasonic energy when it is positioned. By way of example, the bubble in a marker can be formed by introducing air by a syringe (not shown) penetrating the wall of the delivery catheter sheath of said lead extraction system and thereafter is sealed by epoxy.

By way of illustration, a lead extraction system of this invention is inserted along or sliding over the existing lead wire through a vein. By assistance of ultrasonic markers, the system is positioned near the target tissue site where the lead contacted the tissue. The tip section of the multiple-jaw electrodes means is deployed and the ends of the electrodes firmly contact the tissue to be ablated. By employing the electrodes deployment means and the RF energy delivery, the electrodes cut loose the tissue, mainly the scar tissue surrounding the lead. After that, a locking stylet is deployed to securely engage the stylet with the lead wire. The lead is thereafter removed with ease.

From the foregoing, it should now be appreciated that an improved lead extraction system comprising multiple jaw electrodes with ultrasonic imaging capabilities and locking stylet means has been disclosed for removing the implanted lead from a patient. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A lead extraction system comprising:
   a catheter sheath having a distal tip section, a distal end, a proximal end, and at least one lumen extending therebetween;
   a handle attached to the proximal end of the catheter sheath;
   a locking stylet located within the lumen of said catheter sheath; and
   an electrode deployment means including a retractable tip section, comprising a set of deployable jaw electrodes each having a sharp end.

2. The lead extraction system as in claim 1, further comprising RF energy is delivered to the deployable jaw electrodes.

3. The lead extraction system as in claim 2, further comprising fluid being supplied to the distal tip section of the catheter sheath and disposed out of the hollow opening at the distal end of the multiple-jaw electrodes means.

4. The lead extraction system as in claim 3, further comprising fluid being selected from the group of saline, heparin, antibiotics, chemotherapy and therapeutics fluids.

5. The lead extraction system as in claim 4, further comprising a method and system for controlling the flow rate of fluid through the lumen to optimize the cooling of the electrode of the catheter, wherein the control system preferably regulates the flow rate based on signals representative of the temperature of the catheter tip and/or tissue impedance.

6. The lead extraction system as in claim 2, further comprising an electrode deployment means positioned at the distal end of said catheter sheath, wherein said electrode deployment means including a retractable tip section, comprising a non-deployed state for said retractable tip section when said tip section being positioned in the catheter sheath, and further comprising a distended deployed state for said retractable tip section when said tip section being advanced out of the distal end of said catheter sheath.

7. The lead extraction system as in claim 6, further comprising a preformed shape for said deployed tip section, whereby a set of multiple jaw electrodes on said tip section extending outwardly to each respective side of said catheter sheath when being deployed.

8. The lead extraction system as in claim 2, further comprising at least one deployable jaw electrode having a sharp side edge.

9. The lead extraction system as in claim 2, further comprising at least one deployable jaw electrode having a sharp end, wherein said sharp end comprises plurality of sharp points.

10. The lead extraction system as in claim 2, further comprising at least one temperature sensing means and a close-loop temperature control mechanism for the lead extraction system.

11. The lead extraction system as in claim 2, further comprising at least one ultrasonic visible marker being disposed at the distal tip section.

12. The lead extraction system as in claim 2, further comprising the material of the electrode being selected from the group of platinum, iridium, gold, silver, stainless steel, and Nitinol.

13. A method for operating a lead extraction system having a distal tip section under a non-deployed state, into the body, comprising:
   (a) sliding the system over an existing lead wire;
   (b) using the ultrasonic viewing markers to locate the target tissue;
   (c) intimately contacting the distal end of the catheter sheath with the target tissue;
   (d) deploying the multiple-jaw electrodes means;
   (e) applying RF energy to the electrodes while cutting through the tissue;
   (f) engaging the locking stylet onto the lead wire; and
   (g) extracting the lead by pulling the system out of a patient.

14. The method for operating the lead extraction system as in claim 13, further comprising fluid being supplied to the distal tip section of the catheter sheath and disposed out of the opening.

15. A lead extraction application using a lead extraction system comprising:
- a catheter sheath having a distal tip section, a distal end, a proximal end, and at least one lumen extending therebetween;
- a handle attached to the proximal end of the catheter sheath;
- a locking stylet located within the lumen of said catheter sheath;
- an electrode deployment means including a retractable tip section, comprising a set of deployable jaw electrodes each having a sharp end; and
- applying RF energy to said electrodes.

16. The lead extraction application as in claim 15, further comprising fluid being supplied to the distal tip section of the catheter sheath and disposed out of the opening.

17. The lead extraction application as in claim 15, further comprising fluid being selected from the group of saline, heparin, antibiotics, chemotherapy and therapeutics fluids.

18. The lead extraction application as in claim 15, further comprising an electrode deployment means positioned at the distal end of said catheter sheath, wherein said electrode deployment means including a retractable tip section, comprising a non-deployed state for said retractable tip section when said tip section being positioned in the catheter sheath, and further comprising a distended deployed state for said retractable tip section when said tip section being advanced out of the distal end of said catheter sheath.

19. The lead extraction application as in claim 18, further comprising a preformed shape for said deployed tip section, whereby a set of multiple jaw electrodes on said tip section extending outwardly to each respective side of said catheter sheath when being deployed.

20. The lead extraction application as in claim 15, further comprising at least one ultrasonic visible marker being disposed at the distal tip section.

* * * * *